United States Patent
Edwards, III et al.

(10) Patent No.: US 6,541,482 B2
(45) Date of Patent: *Apr. 1, 2003

(54) CARBOCYCLIC NUCLEOSIDE AGENTS USEFUL AS SELECTIVE INHIBITORS OF PROINFLAMMATORY CYTOKINES

(76) Inventors: Carl K. Edwards, III, 1620 S. Pitkin Ave., Superior, CO (US) 80027; David R Borcherding, 8080 N. Delaware Dr., Bangor, PA (US) 18013

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 201 days.

(21) Appl. No.: 08/383,339

(22) Filed: Feb. 3, 1995

(65) Prior Publication Data

US 2002/0004508 A1 Jan. 10, 2002

Related U.S. Application Data

(63) Continuation-in-part of application No. 08/080,249, filed on Jun. 21, 1993, now abandoned.

(51) Int. Cl.⁷ .................... C07D 473/34; C07D 473/16; C07D 473/40; A61K 31/52
(52) U.S. Cl. .................... 514/263.4; 544/264; 544/277; 546/118
(58) Field of Search ................ 544/264, 277; 514/261, 263.4

(56) References Cited

U.S. PATENT DOCUMENTS

| | | | |
|---|---|---|---|
| 4,916,224 A | 4/1990 | Vince et al. | 544/276 |
| 4,931,559 A | 6/1990 | Vince et al. | 544/276 |
| 4,968,674 A | 11/1990 | Taniyama et al. | 544/276 |
| 5,034,394 A | 7/1991 | Daluge | 544/277 |
| 6,156,893 A * | 12/2000 | Bernegger et al. | 544/277 |
| 6,172,224 B1 * | 1/2001 | Kataoka et al. | 544/277 |

FOREIGN PATENT DOCUMENTS

| | | |
|---|---|---|
| EP | 0236935 | 9/1987 |
| EP | 0325460 | 7/1989 |
| EP | 0475411 | 3/1992 |
| EP | 0475413 | 3/1992 |
| EP | 0545413 | 6/1993 |
| WO | 9317020 | 9/1993 |

OTHER PUBLICATIONS

Grant's and Hackh's Chemical Dictionary, 5th Edition, p. 431, 1989.*
Hawley's Condensed Chemical Dictionary, 12th Edition, p. 883, 1996.*
Streiter et al., Cellular and Molecular Regulation of Tumor Necorsis Factor–Alpha Production by Pentoxifylline, Biochem. and Biophysical Research Comm., 155(3):1230–1236 (Sep. 30, 1988).
Coward, J. Med. Chem. 16, 460 (1973).
Vince, J. Med. Chem 33, 17–21 (1990).
S. Okusawa et al., J. Clin. Invest. vol. 81, 1162–1172 (1988).
Dinarello, The J. of Infectious Diseases 163, pp 1177–1184 (1991).
Craig, Bioworld Today, pp 1,3 (Jul. 14, 1994).
Craig, Bioworld Today, pp 1,6 (Jul. 25, 1994).
Tracey, J. Clin. Invest 86: 2014 (1990).
Grant & Hackh'sChemical Dictionary, Fifth Ed., Grant,R. and Grant, C. eds, McGraw–Hill Book Co., New York, p. 431.
Hawley's Condensed Chemical Dictionary, Twelfth Ed., Lewis, R. J., Sr. eds, Van Nostrand Reinhold Co., New York, p. 431.

* cited by examiner

Primary Examiner—Mark L Berch
(74) Attorney, Agent, or Firm—Paul R. Darkes; T. Helen Payne

(57) ABSTRACT

The present invention relates to compounds of the formula

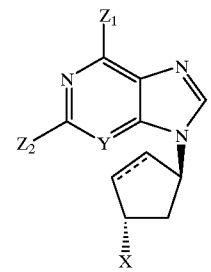

wherein

X is $N_3$, $NH_2$, NHR, $N(R)_2$, CN, SH, SR, or $OR_1$; R is $C_1$–$C_4$ alkyl or $(CH_2)_n$—φ; n is an integer 0, 1, 2, 3 or 4; φ is a phenyl group unsubstituted or substituted with from 1 to 3 substituents, each substituent is independently selected from the group consisting of $C_1$–$C_4$ alkyl, $C_1$–$C_4$ alkoxy, halogen, $CF_3$, $OCF_3$, OH, CN, $NO_2$ or $NH_2$; $R_1$ is $C_1$–$C_4$ alkyl or $(CH_2)_m$—$NR_2R_3$; m is an integer 1, 2, 3 or 4; $R_2$ and $R_3$ are each independently $C_1$–$C_4$ fluorinated akyl or cycloalkyl;

The X substituent on the cyclopentanyl ring is in the TRANS configuration relative to the bicyclic substituent;

Y is nitrogen;

$Z_1$ and $Z_2$ are each independently hydrogen, halogen or $NH_2$; and

---- represents a singe or double bond;

or pharmaceutically acceptable salts thereof, compositions comprising such compounds, and methods of treatment comprising administering of such compounds.

22 Claims, No Drawings

CARBOCYCLIC NUCLEOSIDE AGENTS USEFUL AS SELECTIVE INHIBITORS OF PROINFLAMMATORY CYTOKINES

This is a continuation-in-part of application Ser. No. 08/080,249, filed Jun. 21, 1993 ABN.

BACKGROUND OF THE INVENTION

Autoimmune and inflammatory diseases affect more than fifty million Americans. As a result of basic research in molecular and cellular immunology over the last ten to fifteen years, approaches to diagnosing, treating and preventing these immunological based diseases has been changed forever. By dissecting the individual components of the immune system, those cells, receptors and mediators which are critical to the initiation and progression of immune responses have been, and continue to be, elucidated. Crystallographic analysis of proteins encoded in the major histocompatability complex, identification of an antigen-specific T cell receptor, and development of a basic understanding of the complex cytokine network have all contributed to a revolution in immunology. Equipped with this new and fundamental information about basic immune mechanisms, selective and rational approaches to the treatment of inflammatory and autoimmune disease can now be developed.

Until the last decade, treatment of immunological based disorders were treated exclusively with nonspecific immunosuppressive agents. These included a variety of drugs, such as corticosteroids, antimalarials, methotrexate, azathioprine, and treatments such as total lymphoid irradiation. Although some of these approaches may affect one component of the immune response more than another, they remain nonspecific in their actions and treatment frequently is complicated by serious side effects. It would be very useful to discover and develop new drugs which are immune cell selective or mediator specific and which interfere with processes critical to the initiation, progression, and maintenance of the acute and chronic inflammatory processes associated with certain immunological based diseases.

The two most important cells of the immune response in the autoimmune and inflammatory processes are the T lymphocyte and the monocyte/macrophage.

The T cell is critical to all antigen driven cellular immune responses. There are at least two major subpopulations of T cells: T helper (CD4$^+$) and T cytotoxic (CD8$^+$). T cells recognize antigen via a unique membrane receptor: the T cell antigen receptor (TCR). The TCR can recognize antigen only in association with cell surface proteins known as major histocompatibility complex (MHC) molecules. In response to antigen presented by MHC class II molecules, T helper cells secrete a variety of soluble factors, collectively known as lymphokines. Lymphokines play an essential role in the activation, differentiation, and expansion of all the cells of the immune response. In contrast to the T helper cell, the T cytotoxic cell responds to antigen in one context of MHC class I molecules. Cytotoxic T lymphocytes, once activated, can eliminate cells displaying a specific antigen derived from a virus, tumor cell, or foreign tissue graft.

Mononuclear phagocytic macrophages are widely distributed throughout the body and display great structural and functional heterogeneity. Macrophages are derived from circulating monocytes which migrate into extravascular tissues. The migration of peripheral blood monocytes involves adherence to the endothelium, migration between endothelial cells, and subsequently movement through subendothelial structures. Adherence of monocytes to endothelium involves high molecular weight glycoproteins, such as lymphocyte function-associates antigen 1 (LFA-1; CD11a/CD18), which interacts with intercellular adhesion molecule-1 (ICAM-1; CD54) present on vascular endothelial cells. Monocytes and macrophages produce a variety or pro-inflammatory mediators (cytokines), such as interleukin-1 (IL-1), interleukin-6 (IL-6) and tumor necrosis factor (TNF). These cytokines have numerous effects on many cells within and outside the immune system, such as promoting activation, differentiation, expansion, or apoptosis. In addition, cytokines such as IL-1 increase the expression of adhesion molecules like ICAM-1 and greatly facilitate monocyte migration to the inflammatory site. Furthermore, the monocyte/macrophage is one of the major types of antigen presenting cells required for T helper cell activation.

During the last decade, an understanding of immunopathological reactions has greatly evolved as a result of the characterization of cytokines and interleukins which regulate interactions between cells of the immune system and other nonimmune tissues and cells such as endothelial cells, fibroblasts and adipocytes. A major cytokine increasingly recognized as a central mediator in a wide spectrum of physiologic and immune functions is macrophage-derived Tumor Necrosis Factor-α, also known as TNF-α, or Cachectin. TNF-α has been found to mediate effects as diverse as tumoricidal activity, wasting and weight loss associated with chronic disease, promotion of cartilage erosion and the destruction of joints in rheumatoid arthritis, and the recruitment of cells to participate more effectively in the host's response to an invasive agent. In addition, an increasingly large body of evidence indicates that TNF-α serves as the proximal mediator in the evolution of septic shock.

The biological function of TNF-α extends well beyond its initial discovery as a mediator of tumor necrosis. It is increasingly realized that the interacting milieu of host cytokines existing locally and systemically is an extremely important network that dictates the pathogenesis of many immune and inflammatory diseases. TNF-α appears to play a critically important role in this regard because of its ability to activate a wide range of cell types in order to promote production of several key cytokines (e.g. IL-1β, IL-1α and IL-6), bioactive eicosanoids, and platelet activating factor (PAF).

Enhanced synthesis and release of cytokines has been observed during many acute and chronic inflammatory processes, and it is increasingly realized that in many cases, overproduction of TNF-α is a major contributor to inflammation, cellular injury, and cell death associated with various immunological based diseases.

There is now evidence to indicate that TNF-α is a primary mediator of septic shock. TNF-α, along with other cytokines, triggers inflammatory and metabolic responses attributed to sepsis and septic shock including adult respiratory distress syndrome (ARDS), fever, cachexia, and disseminated intravascular coagulation. ARDS is characterized by increased pulmonary capillary permeability resulting in noncardiogenic pulmonary edema, decreased lung compliance and decreased lung volume. Although ARDS is frequently associated with sepsis, it also occurs as a result of smoke inhalation, pancreatitis and long-bone fractures.

Patients infected with the human immunodeficiency virus (HIV) enter a long period of clinical latency prior to developing clinically apparent disease. HIV infects T cells as well as monocytes and macrophages, and activation of latent or marginally active HIV infected cells may be promoted in part by cytokines, including TNP-α. TNF-α has also been implicated in the pathogenesis of fever, cachexia (wasting syndrome), and Myobacterium tuberculosis infections in patients with acquired immunodeficiency syndrome (AIDS).

Cytokines, including TNF-α, are known to play an important role in the pathogenic processes of inflammatory bowel disease. Ulcerative colitis and Crohn's disease are two common forms of inflammatory bowel disease.

Complex patterns of interacting cytokines, including TNF-α, and products of arachidonic acid metabolism produced locally in the central nervous system have been implicated in contributing to adverse sequelae of bacterial meningitis.

Rheumatoid arthritis is a heterogenous, systemic disease of unknown etiology, and persons with rheumatoid arthritis typically develop inflammation of joint synovium (synovitis). Clinical symptoms become apparent with progression of synovitis due to production and release of cytokines from activated macrophages along with activation of T lymphocytes, angiogenesis, and attraction of neutrophils to the joint cavities. Cytokines induce synovial cell proliferation, resulting in invasion and destruction of articular cartilage. Synovial fibroblasts are thought to become activated by proinflammatory mediators such as TNF-α to secrete a large variety of cytokines and growth factors. TNF-α activity in rheumatoid arthritis includes recruitment and activation of PMNL leukocytes, cellular proliferation, increased prostaglandin and matrix-degrading protease activity, fever, and bone and cartilage resorption. TNF-α and TNF-α-induced IL-1 induce synthesis of collagenase and stromelysin by synoviocytes, contributing to loss of normal joint integrity and function.

Other diseases/syndromes in which TNF-α is implicated are vascular injury/atherosclerosis, diabetes mellitus type I, Kawasaki disease, leprosy, multiple sclerosis, anemia of chronic disease, ultraviolet radiation, Helicobacter pylori gastritis/ulcer disease, paracoccidioidomycosis, septic melioidosis, heart failure, familial Mediterranean fever, toxic shock syndrome, chronic fatigue syndrome, allograft rejection, Graft-versus-host disease, Schistosomiasis.

Thus, it would be very useful to provide a means for inhibition of TNF-α activity in a variety of disease states. The present invention now provides a means for inhibition of TNF-α activity. This provides a treatment for patients suffering from acute and chronic inflammatory processes associated with various immunological based diseases including septic shock. ARDS, inflammatory bowel disease including ulcerative colitis and Chrohn's disease, bacterial meningitis, rheumatoid arthritis, fever/cachexia (wasting syndrome)/Myobacterium tuberculosis infections in patients with AIDS, vascular injury/atherosclerosis, diabetes mellitus A type I, Kawasaki disease, leprosy, multiple sclerosis, anemia of chronic disease, ultraviolet radiation, Helicobacter pylori gastritis/ulcer disease, paracoccidioidomycosis, septic melioidosis, heart failure, familial Mediterranean fever, toxic shock syndrome, chronic fatigue syndrome, allograft rejection, Graft-versus-host disease, Schistosomiasis. In addition, the present invention provides a treatment which inhibits the activation of latent or marginally active HIV infected cells in patients with AIDS.

SUMMARY OF THE INVENTION

The present invention provides compounds having the following general formula (I):

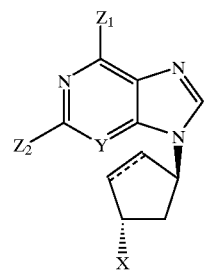

formula (I)

wherein
X is $N_3$, $NH_2$, NHR, $N(R)_2$, CN, $CH_2NH_2$, $CONH_2$, $CO_2H$, $CH_2OH$, SH, SR or $OR_1$; R is $C_1$–$C_4$ alkyl or $(CH_2)_n$—φ; n is an integer 0, 1, 2, 3 or 4; φ is a phenyl group unsubstituted or substituted with from 1 to 3 substituents, each substituent is independently selected from the group consisting of $C_1$–$C_4$ alkyl, $C_1$–$C_4$ alkoxy, halogen, $CF_3$, $OCF_3$, OH, CN, $NO_2$ or $NH_2$; $R_1$ is $C_1$–$C_4$ alkyl or $(CH_2)_m$—$NR_2R_3$; m is an integer 1, 2, 3 or 4; $R_2$ and $R_3$ are each independently $C_1$–$C_4$ alkyl, $C_1$–$C_4$ fluorinated alkyl or cycloalkyl;

the X substituent on the cyclopentanyl ring is in the TRANS configuration relative to the bicyclic substituent;
Y is nitrogen or a CH group;
$Z_1$ and $Z_2$ are each independently hydrogen, halogen or $NH_2$; and
---- represents a single or double bond;
or a pharmaceutically acceptable salt thereof.

The present invention further provides compounds having the following general formula (II);
wherein
Q is methanesulfonate, trifluoromethanesulfonate, p-toluenesulfonate, 2-nitrobenzenesulfonate, 3-nitrobenzenesulfonate, 4-nitrobenzenesulfonate or 4-bromobezenesulfonate;

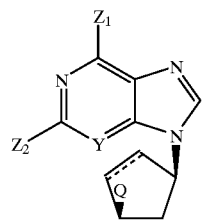

formula (II)

Q is in the CIS configuration relative to the bicyclic substituent;
Y is nitrogen or a CH group;
$Z_1$ and $Z_2$ are each independently hydrogen, halogen or $NH_2$; and
---- represents a single or double bond;
or a pharmaceutically acceptable salt thereof.

The present invention also provides a method of inhibiting the TNF-α activity in a patient in need thereof comprising administering to said patient an effective antiinflammatory amount of a compound of formula I.

The present invention further provides a method of treating a patient suffering from septic shockcomprising administering to said patient an effective antiinflammatory amount of a compound of formula I.

DETAILED DESCRIPTION OF THE INVENTION a) As used herein the term "$C_1$–$C_4$ alkyl" refers to a saturated straight or branched chain hydrocarbon radical of one to four carbon atoms. Included within the scope of this term are methyl, ethyl, n-propyl, isopropyl, n-butyl, isobutyl, and the like.

b) The term "$C_1$–$C_4$ alkoxy" refers an alkyloxy radical made up of an oxygen radical bearing an saturated straight or branched chain hydrocarbon radical of one to four carbon atoms. Included within the scope of this term are methoxy, ethoxy, propyloxy, isopropyloxy, n-butyloxy, isobutyloxy, sec-butyloxy, t-butyloxy and the like.

c) The term "halogen" or "halo" refers to a chlorine, bromine or iodine atom.

d) The term "Lg" refers to a leaving group such as methanesulfonate, trifluoromethanesulfonate, p-toluenesulfonate, 2-nitrobenzenesulfonate, 3-nitrobenzenesulfonate, 4-nitrobenzenesulfonate or 4-bromobezenesulfonate and the like.

e) The term "cycloalkyl" refers to a cycloalkyl radical containing from 3–7 carbon atoms such as cyclopropyl, cyclobutyl, cyclopentyl, cyclohexyl, cycloheptyl and the like.

f) The term "$C_1$–$C_4$ fluorinated alkyl" refers to a fluorinated alkyl radical of from one to four carbon atoms such as trifluoromethyl, 1,1,1-trifluorethyl, 2-fluoroethyl, 1,3-difluoropropyl and the like.

g) The term "φ" refers to a phenyl group unsubstituted or substituted with from 1 to 3 substituents, each substituent independently selected from the group consisting of $C_1$–$C_4$ alkyl, $C_1$–$C_4$ alkoxy, halogen, $CF_3$, $OCF_3$, OH, CN, $NO_2$ or $NH_2$. These substituents may be the same or different and may be located at any of the ortho, meta, or para positions.

h) The term "$(CH_2)_n$—φ" refers to a phenylalkyl substituent wherein n is an integer 0, 1, 2, 3 or 4 and φ is described in (g) above. Included within the scope of this term are benzyl, 2-nitrobenzyl, 2-aminobenzyl, 2-methylbenzyl, 3-methylbenzyl, 4-methylbenzyl, 3,4-dimethoxybenzyl, 2,5-dimethylbenzyl, 3,4-dimethylbenzyl, 4-tert-butylbenzyl, 2-chlorobenzyl, 3-chlorobenzyl, 4-chlorobenzyl, 4-cyanobenzyl, 4-trifluoromethoxybenzyl, 2-trifluoromethylbenzyl, 3-trifluoromethylbenzyl, 2-(p-chlorophenyl) ethyl, 2-(p-methoxyphenyl)ethyl, 3-(p-chlorophenyl)propyl, 3-(p-methoxyphenyl)propyl, 3-phenylpropyl and the like.

i) The term "$(CH_2)_m$-$NR_2R_3$" refers to an alkylamino substituent wherein m is an integer 1, 2, 3 or 4 and $R_2$ and $R_3$ are each independently $C_1$–$C_4$ alkyl (defined in (a) above), $C_1$–$C_4$ fluorinated alkyl (defined in (f) above) or cycloalkyl (defined in (e) above). Included within the scope of this term are 2-dimethylaminoethyl, 2-diethylaminoethyl, 3-dimethylaminopropyl, 2-(dipropylamino)ethyl, 2-(dibutylamino)ethyl, 3-diethylamino-1-propyl and the like.

j) The term "pharmaceutically acceptable salt" refers to those salts that are not substantially toxic at the dosage administered to achieve the desired effect and do not independently possess significant pharmacological activity. The salts included within the scope of this term are hydrobromide, hydrochloride, sulfuric, phosphoric, nitric, formic, acetic, propionic, succinic, glycolic, lactic, malic, tartaric, citric, ascorbic, α-ketoglutaric, glutamic, aspartic, maleic, hydroxymaleic, pyruvic, phenylacetic, benzoic, p-aminobenzoic, anthranilic, p-hydroxybenzoic, salicyclic, hydroxyethanesulfonic, ethylenesulfonic, halobenzenesulfonic, toluenesulfonic, naphthalenesulfonic, methanesulfonic, sulfanilic, and the like. Hydrochloride is preferred as the pharmaceutically acceptable salt of compounds of formulas (I) and (II).

It is understood that the X substituent on the cyclopentanyl ring of the compounds of formula I have a TRANS configuration relative to the bicyclic substituent. It is further understood that the compounds of formula (I) may exist in a variety of stereoisomeric configurations wherein the compounds of formula (I) contain 2 chiral centers resulting in the possibility of four stereoisomers being present. The chiral centers are located at position 1 and position 3 on the cyclopentanyl substituent of formula (I). These stereoisomers are specifically understood to be included within the scope of the present invention.

It is further understood that the Q substituent on the cyclopentanyl ring of the compounds of formula (II) have a CIS configuration relative to the bicyclic substituent. It is further understood that these compounds of formula (II) may exist in a variety of stereoisomeric configurations wherein the compounds of formula (II) contain 2 chiral centers resulting in the possibility of four stereoisomers being present. The chiral centers are located at position 1 and position 3 on the cyclopentanyl substituent of formula (II). These stereoisomers are specifically understood to be included within the scope of the present invention.

The compounds of formula (I) wherein X is $N_3$, NHR, $N(R)_2$, CN, SH, SR or $OR_1$ and of formula (II) can be prepared as described in Scheme I. All other substituents, unless otherwise indicated, are previously defined. The reagents and starting materials are readily available to one of ordinary skill in the art.

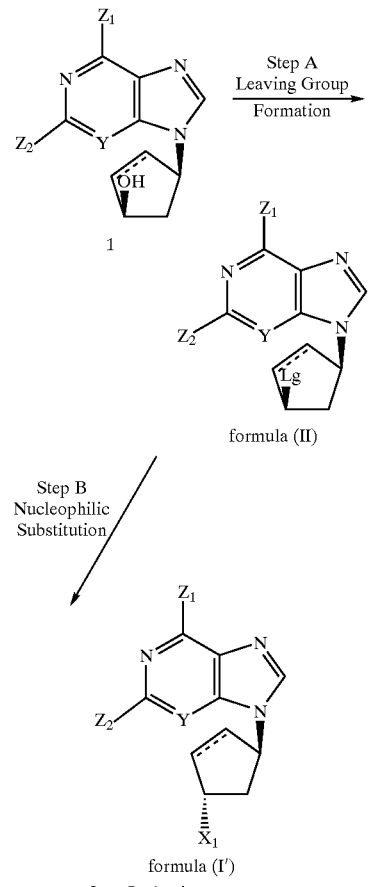

Scheme I

Lg = Q = leaving group
$X_1$ = $N_3$, NHR, $N(R)_2$, CN, SH, SR and $OR_1$.

In Scheme I, the CIS-hydroxy derivatives defined by structure (1) may be prepared by chemical reactions analogously known in the art, such as that disclosed by Borcherding et al. in European Patent Application Publication No. 0 475 411 published Mar. 18, 1992 and European Patent Application Publication No. 0 475 413 published Mar. 18, 1992. In step A, the 3'-Cis-hydroxy derivative of structure (1) is treated with a suitable sulfonyl chloride to provide the sulfonate derivative described by formula (II).

For example, the 3'-Cis hydroxy derivative of structure (1), such as 1R, 3S-cis-1-(9-adenyl)-hydroxycyclopentane is dissolved in a suitable organic solvent mixture, such as methylene chloride and tetrahydrofuran (5:3). An excess of a suitable sulfonyl chloride is added. Examples of a suitable sulfonyl chloride are methanesulfonyl chloride, trifluoromethanesulfonyl chloride, p-toluenesulfonyl chloride, 2-nitrobenzenesulfonyl chloride, 3-nitrobenzenesulfonyl chloride, 4-nitrobenzenesulfonyl chloride or 4-bromobezenesulfonyl chloride. The preferred sulfonyl chloride is methanesulfonyl chloride. Triethylamine is added and the reaction is stirred for 30 minutes to 3 hours. The reaction is then quenched with water and extracted with a suitable organic solvent, such as methylene chloride. The combined organic extracts are dried over a suitable drying agent, such as anhydrous sodium sulfate, filtered and concentrated under vacuum to provide the sulfonate derivative described by formula (II).

In Scheme I, step B the sulfonate derivative of formula (II) can undergo a nucleophilic substitution by treatment with a suitable nucleophile to provide the compounds described by structure (2) which have the TRANS configuration relative to the bicyclic substituent.

For example, a sulfonate derivative of formula (II), such as 1R, 3S-cis-1-(9-adenyl)-3-methanesulfoxycyclopentane is dissolved in a suitable organic solvent, such as ethanol, dimethylsulfoxide or dimethylformamide and treated with an excess of a suitable nucleophile. Examples of suitable nucleophiles include sodium azide, sodium cyanide, potassium cyanide, lithium cyanide, methylamine, dimethylamine, methyl mercaptide, sodium hydrosulfide, sodium 2-dimethylamino-1-ethoxide, potassium phthalimide, potassium thioacetate and the like. The reaction is stirred at room temperature for approximately 24 hours and then heated at reflux for 2 to 6 hours. Alternatively the reaction can be directly heated at reflux for 2 to 6 hours. The reaction is then concentrated under vacuum and the residue is purified by techniques well known to one skilled in the art. For example, the residue is dissolved in a suitable organic solvent mixture, such as methylene chloride:methanol (9:1) and passed through a plug of silica gel. The filtrate is then concentrated under vacuum to provide the nucleophilic substitution product described by formula (I').

The compounds of the formula (I) wherein X is $CH_2NH_2$, $CO_2H$, $CONH_2$ and $CH_2OH$ can be prepared as described in Scheme II. All other substituents, unless otherwise indicated, are previously defined. The reagents and starting materials are readily available to one of ordinary skill in the art.

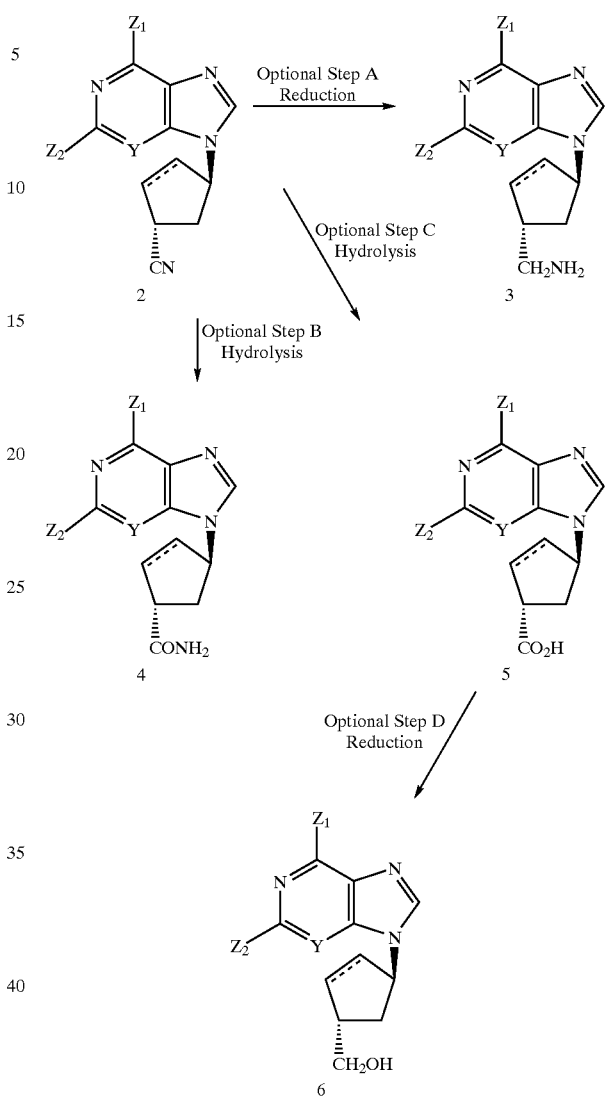

Scheme II

In Scheme II, optional step A the cyano compound (prepared in Scheme I) described by structure (2) is reduced to the appropriately substituted aminomethyl compound described by structure (4).

For example, the cyano compound described by structure (2), such as 1R,3R-trans-1-(9-adenyl)-3-cyanocyclopentane, is dissolved in a suitable solvent, such as tetrahydrofuran and treated with an excess of a suitable reducing agent, such as 2M aluminum hydride in tetrahydrofuran. The reaction is refluxed for 2 to 6 hours. Excess reducing agent is carefully decomposed by treatment with acetone and then acidified to pH 7. The mixture is then filtered and the filtrate is concentrated under vacuum. The residue is purified by techniques well known to one skilled in the art. For example, the residue is purified by flash chromatography on silica gel with methylene chloride:methanol (17:3) as eluent to provide the 1R,3R-trans-1-(9-adenyl)-3-aminomethylcyclopentane described by structure (3).

In Scheme II, optional step B the cyano compound described by structure (2) is hydrolyzed to the appropriately substituted amide described by structure (4).

For example, the cyano compound described by structure (2), such as 1R,3R-trans-1-(9-adenyl)-3-cyanocyclopentane is dissolved in a suitable solvent, such as methanol and treated with an equivalent of a suitable base, such as potassium hydroxide. The reaction is heated at reflux for 1 to 5 hours and then concentrated under vacuum. The residue is then purified by techniques well known in the art. For example the residue can be purified by flash chromatography on silica gel utilizing a suitable eluent, such as methylene chloride:methanol to provide the purified amide (4).

In Scheme II, optional step C the cyano compound described by structure (2) is hydrolyzed to the appropriately substituted acid described by structure (5).

For example, the cyano compound described by structure (2), such as 1R,3R-trans-1-(9-adenyl)-3-cyanocyclopentane is dissolved in a suitable organic solvent, such as tetrahydrofuran. An excess of a suitable base, such as potassium hydroxide is added and the reaction is heated at reflux for approximately 6 hours. After cooling, the reaction is neutralized with a suitable acid, such as 6N hydrochloric acid and the product purified by techniques well known to one skilled in the art. For example, the product can be isolated by ion exchange chromatography to provide the 1R,3R-trans-1-(9-adenyl)cyclopentane-3-carboxylic acid described by structure (5).

In Scheme II, step D the carboxylic acid described by structure (5) is reduced to the appropriately substituted alcohol described by structure (6).

For example, the carboxylic acid described by structure (5), such as 1R,3R-trans-1-(9-adenyl)cyclopentane-3-carboxylic acid is dissolved in a suitable organic solvent, such as tetrahydrofuran. An excess of a suitable reducing agent, Such as 2M lithium aluminum hydride in tetrahydrofuran is added dropwise to the reaction. The reaction is heated at reflux for 2 to 6 hours. After cooling, excess reducing agent is decomposed by treatment with acetone followed by dilute hydrochloric acid to adjust to pH 7. The mixture is then filtered and the filtrate is concentrated under vacuum. The residue is then purified by techniques well known to one skilled in the art. For example, the residue can be purified by flash chromatography using methylene chloride:methanol (17:3) as the eluent to provide the 1R,3R-trans-1-(9-adenyl)-3-hydroxymethylcyclopentane described by structure (6).

The compounds of the formula (I) wherein X is $NH_2$ can be prepared as described in Scheme III. All other substituents, unless otherwise indicated, are previously defined. The reagents and starting materials are readily available to one of ordinary skill in the art.

Scheme III

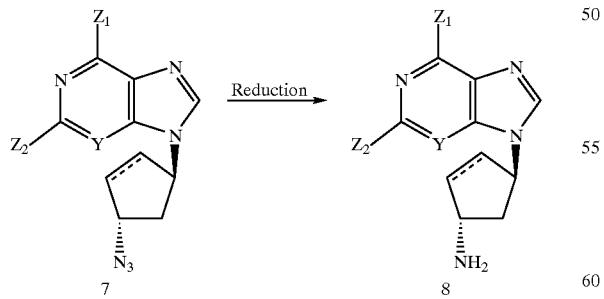

In Scheme III, the azide described by structure (7) whose preparation was previously described in Scheme I, step B, is reduced to the primary amine described by structure (C).

For example, the azide described by structure (7), such as 1R,3R-trans-1-(9-adenyl)-3-azidocyclopentane is dissolved in a suitable organic solvent, such as tetrahydrofuran and treated with an excess of a suitable reducing agent, such as 2M lithium aluminum hydride in tetrahydrofuran. The reaction is heated at reflux for 2 to 6 hours. After cooling, the excess reducing agent is decomposed with water, the mixture is filtered and the filtrate is concentrated under vacuum. The residue is then purified by techniques well known to one skilled in the art. For example, the residue is purified by flash chromatography using silica gel and a suitable organic eluent, such as methylene chloride:methanol (17:3) to provide the 1R,3R-trans-1-(9-adenyl)-3-aminocyclopentane described by structure (8).

The enantiomers of formulas (I) and (II) can be resolved utilizing techniques well known in the art of chemistry such as crystallization techniques described by Jacques, J. et al. "Enantiomers, Racemates, and Resolutions", John Wiley and Sons, Inc., 1981 or by chiral column chromatography.

The following examples present typical syntheses as described by Schemes I, II and III. These examples are understood to be illustrative only and are not intended to limit the scope of the invention in any way. As used in the following examples, the following terms have the meanings indicated: "eq." refers to equivalents, "g" refers to grams, "mg" refers to milligrams, "mmol" refers to millimoles, "mL" refers to milliliters, "° C" refers to degrees Celsius, "TLC" refers to thin layer chromatography, and "δ" refers to parts per million down field from tetramethylsilane.

EXAMPLE 1a

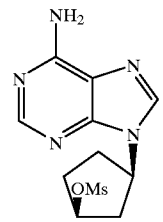

Preparation of 1R,3S-cis-1-(9-adenyl)-3-methanesulfoxycyclopentane.

Scheme I, step A; Dissolve 1R,3S-cis-1-(9-adenyl)-3-hydroxycyclopentane (150 mg, 0.7 mmol) in methylene chloride (15 mL) and tetrahydrofuran (9 mL). Add excess methanesulfonyl chloride and triethylamine and stir for 30 minutes. Add water (50 mL) and separate the layers. Extract the aqueous phase with methylene chloride (50 mL), combine the organic phases and dry over anhydrous sodium sulfate. Filter and concentrate to provide the title compound (190 mg) as a white solid.

EXAMPLE 1b

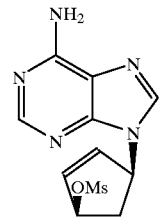

Preparation of 1R,3S-cis-1-(9-adenyl)-3-methanesulfoxy-4-cyclopentene.

Scheme I, step A; In an analogous manner to Example 1a the title compound can be prepared from 1R,3S-cis-1-(9-adenyl)-3-hydroxy-4-cyclopentene.

EXAMPLE 2a

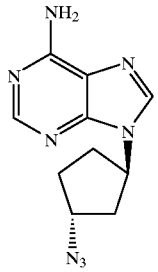

Preparation of 1R,3R-trans-1-(9-adenyl)-3-azidocyclopentane.

Scheme I, step B; Dissolve 1R,3S-cis-1-(9-adenyl)-3-methanesulfoxycyclopentane (170 mg, 0.6 mmol) and lithium azide (60 mg, 1.2 mmol) in ethanol (10 mL). Stir overnight at room temperature and then reflux for three hours. Concentrate the reaction under vacuum and purify the residue by dissolving it in a mixture of methylene chloride:methanol (9:1) and then passing the solution through a silica gel plug. Concentrate the filtrate under vacuum to provide the title compound (120 mg) as a white solid, mp 109.5–110° C.; IR (azide, 2100.61 cm$^{-1}$); $[\alpha]_D$=— 16.8° (c=0.519, methanol); UV=261 nm (H$_2$O); CI/MS (CH$_4$) 245 (M$^{+1}$), 202 (base); $^{13}$C NMR (DMSO-d$_6$) δ156, 152, 149, 139, 119, 61, 53, 38, 30, 29; $^1$H NMR (DMSO-d$_6$) δ8.22 (s, 1H), 8.16 (s, 1H), 7.2 (bs, 2H, exch. D$_2$O), 5.02 (p, 1H), 4.48 (m, 1H), 2.56–2.0 (m, 5H), 1.75 (m, 1H).

EXAMPLE 2b

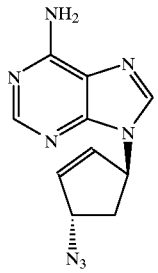

Preparation of 1R,3R-trans-1-(9-adenyl)-3-azido-4-cyclopentene.

Scheme I, step B; In an analogous manner to Example 2a the title compound can be prepared from 1R,3S-cis-1-(9-adenyl)-3-methanesulfoxy-4-cyclopentene.

EXAMPLE 3a

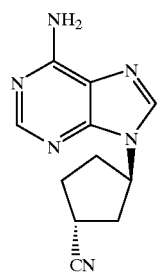

Preparation of 1R,3R-trans-1-(9-adenyl)-3-cyanocyclopentane.

Scheme I, step B; Dissolve 1R,3S-cis-1-(9-adenyl)-3-methanesulfoxycyclopentane (0.6 mmol) and potassium cyanide (1.2 mmol) in dimethylsulfoxide. Heat the reaction at 75° C. for 6 hours and then concentrate under vacuum. Purify in a manner analoguous to example 2a to provide the title compound.

EXAMPLE 3b

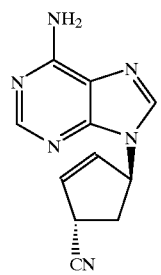

Preparation of 1R,3R-trans-1-(9-adenyl)-3-cyano-4-cyclopentene.

Scheme I, step B; In an analogous manner to Example 3a the title compound can be prepared from 1R,3S-cis-1-(9-adenyl)-3-methanesulfoxy-4-cyclopentene.

EXAMPLE 4a

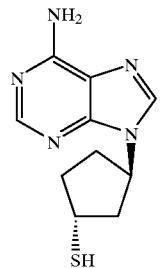

Preparation of 1R,3R-trans-1-(9-adenyl)cyclooentane-3-thiol.

Scheme I, step B; Dissolve 1R,3S-cis-1-(9-adenyl)-3-methanesulfoxycyclopentane (20 mg) and sodium hydrogensulfide (100 mg) in ethanol. Reflux the reaction for three days and then concentrate under vacuum. Purify in a manner analoguous to example 2 to provide the title compound (4 mg). H1-NMR (CD3OD) 8.3 (s, 1H), 8.2 (s, 1H), 5.1 (p, 1H), 4.15 (m, 1H), 2.5–2.25 (m, 4H), 2.2–2.0 (m, 1H), 1.95–1.85 (m, 1H)

EXAMPLE 4b

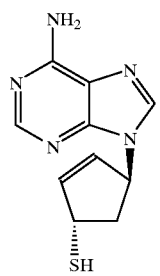

Preparation of 1R,3R-trans-1-t9-adenyl)-4-cyclopentene-3-thiol.

Scheme I, step B; In an analogous manner to Example 4a the title compound can be prepared from 1R,3S-cis-1-(9-adenyl)-3-methanesulfoxy-4-cyclopentene.

EXAMPLE 5a

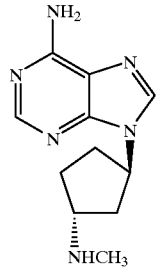

Preparation of 1R,3R-trans-1-(9-adenyl)-3-N-methylaminoclopentane.

Scheme I, step B; Dissolve 1R, 3S-cis-1-(9-adenyl)-3-methanesulfoxycyclopentane (0.6 mmol) and methylamine (1.2 mmol) in ethanol. Reflux the reaction for three hours and then concentrate under vacuum. Purify in a manner analoguous to example 2 to provide the title compound.

EXAMPLE 5b

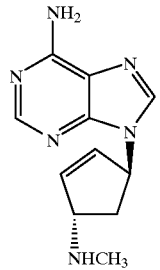

Preparation of 1R,3R-trans-1-(9-adenyl)-3-N-methylamino-4-cyclopentene.

Scheme I, step B; In an analogous manner to Example 5a the title compound can be prepared from 1R,3S-cis-1-(9-adenyl)-3-methanesulfoxy-4-cyclopentene.

EXAMPLE 6a

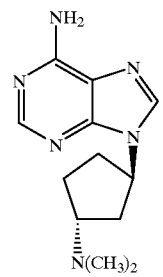

Preparation of 1R,3R-trans-1-(9-adenyl)-3-N,N-dimethylaminocyclopentane.

Scheme I, step B; Dissolve 1R,3S-cis-1-(9-adenyl)-3-methanesulfoxycyclopentane (0.6 mmol) and dimethylamine (1.2 mmol) in ethanol. Reflux the reaction for three hours and then concentrate under vacuum. Purify in a manner analoguous to example 2 to provide the title compound.

EXAMPLE 6b

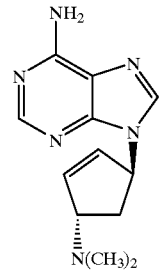

Preparation of 1R,3R-trans-1-(9-adenyl)-3-N,N-dimethylamino-4-cyclopentene.

Scheme I, step B; In an analogous manner to Example 6a the title compound can be prepared from 1R,3S-cis-1-(9-adenyl)-3-methanesulfoxy-4-cyclopentene.

EXAMPLE 7a

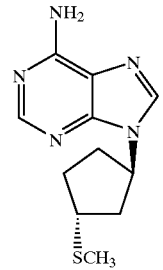

Preparation of 1R,3R-trans-1-(9-adenyl)-3-methxlmercaptocyclopentane.

Scheme I, step B; Combine 1R,3S-cis-1-(9-adenyl)-3-methanesulfoxycyclopentane (0.6 mmol) and potassium hydroxide (1.2 mmol) in methanol. Bubble in methyl mercaptan until the solution is saturated and then reflux for three hours. Concentrate the reaction under vacuum and purify in a manner analoguous to example 2 to provide the title compound.

EXAMPLE 7b

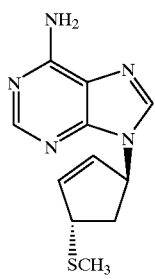

Preparation of 1R,3R-trans-1-(9-adenyl)-3-methylmercapto-4-cyclopentene.

Scheme I, step B; In an analogous manner to Example 7a the title compound can be prepared from 1R,3S-cis-1-(9-adenyl)-3-methanesulfoxy-4-cyclopentene.

EXAMPLE 8a

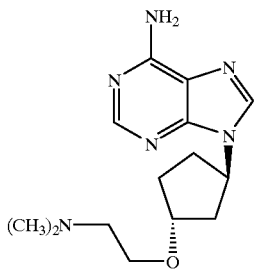

Preparation of 1R,3R-trans-1-(9-adenyl)-3-(2-dimethylamino-1-ethoxy)cyclopentane.

Scheme I, step B; Dissolve 1R,3S-cis-1-(9-adenyl)-3-methanesulfoxycyclopentane (0.6 mmol) and sodium 2-dimethylamino-1-ethoxide (1.2 mmol) in tetrahydrofuran. Reflux the reaction for three hours and then concentrate under vacuum. Purify in a manner analoguous to example 2 to provide the title compound.

EXAMPLE 8b

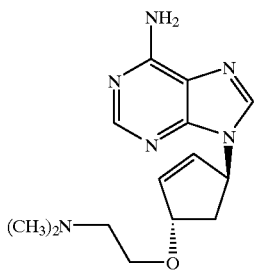

Preparation of 1R,3R-trans-1-(9-adenyl)-3-(2-dimethylamino-1-ethoxy)-4-cyclopentene.

Scheme I, step B; In an analogous manner to Example 8a the title compound can be prepare from 1R,3S-cis-1-(9-adenyl)-3-methanesulfoxy-4-cyclopentene.

EXAMPLE 9a

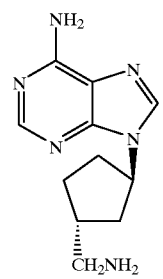

Preparation of 1R,3R-trans-1-(9-adenyl)-3-aminomethylcyclopentane.

Dissolve 1R, 3S-cis-1-(9-adenyl)-3-cyanocyclopentane in tetrahydrofuran and add excess 2M lithium aluminum hydride in tetrahydrofuran dropwise. Reflux for two to six hours. Decompose the excess lithium aluminum hydride, filter and concentrate under vacuum. Purify the residue by flash chromatography (silica gel) using methylene choloride:methanol (17:3) as the eluent to provide the title compound.

EXAMPLE 9b

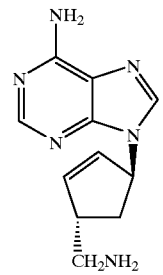

Preparation of 1R,3R-trans-1-(9-adenyl)-3-aminomethyl-4-cyclopentene.

In an analogous manner to Example 9a the title compound can be prepared from 1R,3S-cis-1-(9-adenyl)-3-cyano-4-cyclopentene.

EXAMPLE 10a

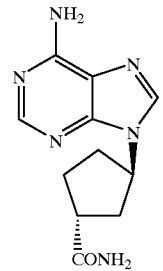

Preparation of 1R,3R-trans-1-(9-adenyl)cyclorentane-3-carboxamide.

Dissolve 1R,3S-cis-1-(9-adenyl)-3-cyanocyclopentane (1 mmol) in methanol and treat with potassium hydroxide (1 mmol). Heat the reaction at reflux for 2 hours. After cooling concentrate under vacuum and purify the residue by flash chromatography (methylene chloride/methanol, 17:3, silica gel) to provide the title compound.

EXAMPLE 10b

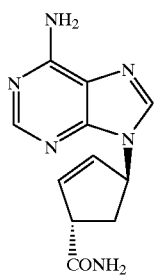

Preparation of 1R,3R-trans-1-(9-adenyl)-4-cyclopentene-3-carboxamide.

In an analogous manner to Example 10a the title compound can be prepared from 1R,3S-cis-1-(9-adenyl)-3-cyano-4-cyclopentene.

EXAMPLE 10c

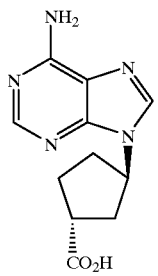

Preparation of 1R,3R-trans-1-(9-adenyl)cyclopentane-3-carboxylic acid.

Dissolve 1R,3S-cis-1-(9-adenyl)-3-cyanocyclopentane in tetrahydrofuran and add excess potassium hydroxide. Reflux for approximately 6 hours. Neutralize the reaction with 6N hydrochloric acid and purify by ion exchange chromatography to provide the title compound.

EXAMPLE 10d

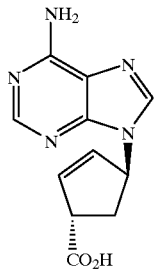

Preparation of 1R,3R-trans-1-(9-adenyl)-4-cyclopentene-3-carboxylic acid.

In an analogous manner to Example 10d the title compound is prepared from 1R,3S-cis-1-(9-adenyl)-3-cyano-4-cyclopentene.

EXAMPLE 11a

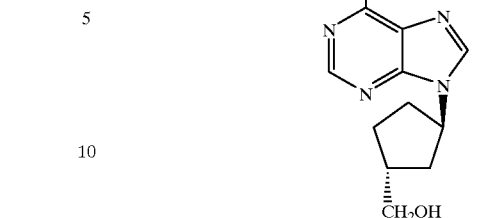

Preparation of 1R,3R-trans-1-(9-adenyl)-3-hydroxymethylcyclopentane.

Dissolve 1R,3S-trans-1-(9-adenyl)cyclopentane-3-carboxylic acid in tetrahydrofuran and add excess 2M lithium aluminum hydride in tetrahydrofuran dropwise. Reflux for two to six hours. Decompose the excess lithium aluminum hydride, filter, concentrate under vacuum and purify in a manner analogous to example 9 to provide the title compound.

EXAMPLE 11b

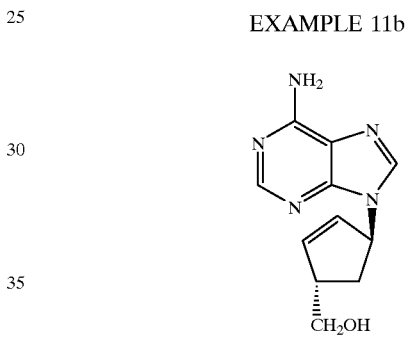

Preparation of 1R,3R-trans-1-(9-adenyl)-3-hydroxymethyl-4-cyclopentene.

In an analogous manner to Example 11a the title compound can be prepared from 1R,3R-trans-1-(9-adenyl)-4-cyclopentene-3-carboxylic acid.

EXAMPLE 12a

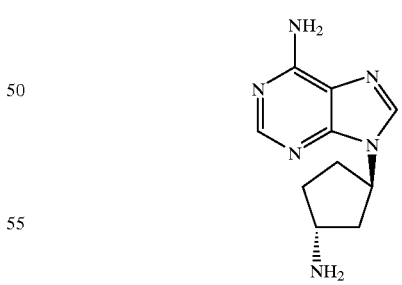

Preparation of 1R,3R-trans-1-(9-adenyl)-3-aminocyclopentane.

Scheme III; Dissolve 1R,3R-trans-1-(9-adenyl)-3-azidocyclo-pentane (15 mg) in tetrahydrofuran (5 ml) and add excess 2M lithium aluminum hydride (112 mg) in tetrahydro-furan (10 ml) dropwise. Reflux for six hours. Decompose the excess lithium aluminum hydride, filter, concentrate under vacuum and purify in a manner analogous to example 9 to provide the title compound (9 mg). H¹-NMR (CD₃OD) 8.23 (s, 2H), 5.18 (p, 1H), 4.13 (p, 1H), 2.7–2.28 (m, 5H), 1.91 (m, 1H).

EXAMPLE 12b

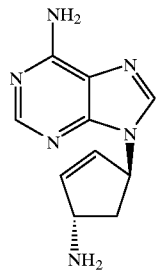

Preparation of 1R,3R-trans-1-(9-adenyl)-3-amino-4-cyclopentene.

Scheme III; In an analogous manner to example 12a the title compound can be prepared from 1R,3R-trans-1-(9-adenyl)-3-azido-4-cyclopentene. The present invention further provides a method of inhibiting TNF-α activity in a patient in need thereof comprising administering to said patient an antiinflammatory amount of a compound of formula (I). The present invention further provides a method of treating a patient suffering from certain autoimmune or other diseases for which elevated activity of TNF-α is implicated as a contributing factor in the progression of the disease comprising administering to said patient a compound of formula (I).

As used herein, the term "patient" refers to a warm-blooded animal such as a mammal which is suffering from, or is in danger of suffering from, an acute or chronic inflammation, cellular injury or cell death associated with an immunological based disease. It is understood that humans, mice and rats are included within the scope of the term "patient".

Administration of a compound of formula (I) to a patient results in a selective antiinflammatory effect in the patient. More specifically, administration of a compound of formula (I) to a patient results in inhibition of TNF-α activity in the patient which selectively inhibits TNF-α-mediated inflammatory events. In other words, by treatment of a patient with a compound of formula (I), the TNF-α-mediated inflammatory response and subsequent inhibition of other cytokines associated with various diseases is inhibited or suppressed over that present in the absence of treatment.

A patient is in need of treatment with an agent which inhibits TNF-α activity, such as a compound of formula (I), where the patient is suffering from certain autoimmune or other diseases for which elevated activity of TNF-α is implicated as a contributing factor in the progression of the disease. The term "autoimmune disease" refers to those disease states and conditions wherein the immune response of the patient is directed against the patient's own constituents resulting in an undesirable and often terribly debilitating condition.

Patients suffering from autoimmune diseases such as mseptic shock, ARDS, inflammatory bowel disease including ulcerative colitis and Chrohn's disease, rheumatoid arthritis, fever/cachexia (wasting syndrome)/Myobacterium tuberculosis infections in patients with AIDS, AIDS, diabetes mellitus type I, Kawasaki disease, multiple sclerosis, familial Mediterranean fever, toxic shock syndrome are in need of treatment with a selective antiinflammatory agent such as a compound of formula (I). In addition, patients suffering from bacterial meningitis, vascular injury/atherosclerosis, leprosy, anemia of chronic disease, ultraviolet radiation, Helicobacter pylori gastritis/ulcer disease, paracoccidioidomycosis, septic melioidosis, heart failure, chronic fatigue syndrome, allograft rejection, Graft-versus-host disease, Schistosomiasis are also in need of treatment with a selective antiinflammatory agent such as a compound of formula (I). As such, treatment of patients suffering from these diseases by administration of a compound of formula (I) will be particularly effective in preventing further deterioration or worsening of the patient's condition. Treatment of a patient at an early stage of an autoimmune disease would be particularly effective in preventing further deterioration of the disease state into a more serious condition.

Patients suffering from septic shock, ARDS, AIDS, fever/cachexia/Myobacterium tuberculosis infection associated with AIDS, inflammatory bowel disease including ulcerative colitis and Chrohn's disease, bacterial meningitis, cachexia, and rheumatoid arthritis are particularly good candidates for treatment with a compound of formula (I).

Based on standard clinical and laboratory tests and procedures, an attending diagnostician, as a person skilled in the art, can readily identify those patients who are in need of treatment with a selective antiinflammatory agent such as a compound of formula (I).

An effective antiinflammatory amount of a compound of formula (I) is that amount which is effective, upon single or multiple dose administration to a patient, in providing an antiinflammatory effect or, more particularly, an inhibition of TNF-α activity. An antiinflammatory effect refers to the slowing, interrupting, inhibiting or preventing the further expression of TNF-α-mediated inflammatory effects.

An effective antiinflammatory amount of a compound of formula (I) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective antiinflammatory amount of a compound of formula (I) is expected to vary from about 0.1 milligram per kilogram of body weight per day (mg/kg/day) to about 500 mg/kg/day. Preferred amounts are expected to vary from about 1 to about 50 mg/kg/day.

In effecting treatment of a patient, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration and intravenous administration are generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (I) in admixture or otherwise in association with one or more inert carriers. These compositions are useful, for example, as assay standards, as convenient means of making bulk shipments, or as pharmaceutical compositions. An assayable amount of a compound of formula (I) is an amount which is readily measurable by standard assay procedures and techniques as are well known and appreciated by those skilled in the art. Assayable amounts of a compound of formula (I) will generally vary from about 0.001% to about 75% of the composition by weight. Inert carriers can be any material which does not degrade or otherwise covalently react with a compound of formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective immunosuppressive amount of a compound of formula (I) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (I) in their end-use application. Compounds of the formula (I) wherein Y is nitrogen are generally preferred. Compounds of the formula (I) wherein $Z_1$ is $NH_2$ and $Z_2$ is hydrogen are generally preferred.

The following specific compounds of formula (I) are especially preferred:

(1R,3R)-Trans-1-(9-adenyl)-3-azidocyclopentane;

(1R,3R)-Trans-1-(9-adenyl)-3-azidocyclopentane hydrochloride;

(1R,3R)-Trans-1-(9-adenyl)cyclopentane-3-thiol; and (1R,3R)-Trans-1-(9-adenyl)-3-aminocyclopentane.

Compounds of formula (II) are useful as chemical intermediates in the synthesis of compounds of formula (I).

The following studies illustrate the utility of the compounds of formula (I). These studies are understood to be illustrative only and are not intended to limit the scope of the invention in any way. As used herein the following terms have the indicated meanings: "$\mu M$" refers to micromolar concentration; "Units" refers to the internationally accepted measurement of protein; "S.D." refers to standard deviation; "ηmol" refers to nanomoles; "ηg" refers to nanograms.

In Vitro Activity

Utilizing an in vitro cellular immunology-based assay which uses human peripheral blood and subsequent purification of monocyte-derived macrophages (according to the method of Edwards et al. *J. Cellular Biochemistry* 1993, 19E: 35), 1R, 3R-TRANS-1-(9-adenyl)-3-azidocyclopentane shows elevated activity in proinflammatory cytokine inhibition. Monocyte-derived macrophages stimulated with bacterial lipopolysaccharide (LPS) produce high levels of TNF-α (14.87±1.02 ηg/mL) during 18 hours of culture. 1R, 3R-TRANS-1-(9-adenyl)-3-azidocyclopentane is effective at inhibiting TNF-α levels in a dose response fashion (500 μM–0.1 μM) with an $IC_{50}$ value of 5.48±1.3 μM in comparison to the positive control compound used in this assay (Pentoxifylline [PTX]; $IC_{50}$= 26.34±16.02 μM).

In Vivo Activity

Utilizing an in vivo immunology-based assay which uses a D-galactosamine animal model of septic shock (according to the method of Parmely et al. *European Cytokine Network*, vol.3, No.2, page 249), 1R, 3R-TRANS-1-(9-adenyl)-3-azidocyclopentane shows elevated activity in protecting mice against the lethal effects of LPS. Mice treated with the vehicle Hanks Balanced Salt Solution (HBSS) approximately 1 hour before intraperitoneal (i.p.) challenge of D-galactosamine and LPS, succumb to disease by 18 hours after challenge (e.g. 6 out of 6 mice killed; 0% protection). However, treating mice with 1R, 3R-TRANS-1-(9-adenyl)-3-azidocyclopentane (100 mg/kg i.p., time=–1 hour) affords significantly (p<0.05 by $X^2$ analysis) enhanced protection (2 out of 6 mice killed; 66% protection). Positive-control PTX afforded decreased protection in this model (3 out of 6 mice killed; 50% protection).

What is claimed is:

1. A compound of the formula

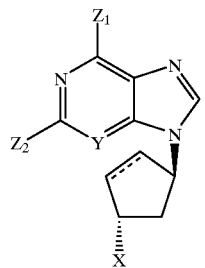

wherein

X is $N_3$, $NH_2$, NHR, $N(R)_2$, CN, SH, SR or $OR_1$; R is $C_1$–$C_4$ alkyl or $(CH_2)_n$—φ; n is an integer 0, 1, 2, 3 or 4; φ is a phenyl group unsubstituted or substituted with from 1 to 3 substituents, each substituent is independently selected from the group consisting of $C_1$–$C_4$ alkyl, $C_1$–$C_4$ alkoxy, halogen, $CF_3$, $OCF_3$, OH, CN, $NO_2$ or $NH_2$; $R_1$ is $C_1$–$C_4$ alkyl or $(CH_2)_m$—$NR_2R_3$; m is an integer 1, 2, 3 or 4; $R_2$ and $R_3$ are each independently $C_1$–$C_4$ alkyl, $C_1$–$C_4$ fluorinated alkyl or cycloalkyl;

The X substituent on the cyclopencanyl ring is in the TRANS configuration relative to the bicyclic substituent;

Y is nitrogen;

$Z_1$ and $Z_2$ are each independently hydrogen, halogen or $NH_2$; and

---- represents a single or double bond;

or a pharmaceutically acceptable salt thereof.

2. A composition comprising a compound according to claim 1 and an inert carrier.

3. The compound according to claim 1, wherein $Z_2$ is hydrogen.

4. The compound according to claim 3, wherein $Z_1$ is $NH_2$.

5. The compound according to claim 1, wherein X is selected from the group consisting of $N_3$, $NH_2$, NHR, $N(R)_2$, CN, SH, SR and $OR_1$ and R is $C_1$–$C_4$alkyl.

6. A composition comprising a compound according to claim 1 and a pharmaceutically acceptable carrier or excipient.

7. The compound according to claim 1, wherein X is $NH_2$.

8. A composition comprising a compound according to claim 1 and an adjuvant.

9. The compound according to claim 5, wherein $Z_2$ is hydrogen.

10. A compound of claim 1, wherein the compound is (1R,3R)-TRANS-1-(9-adenyl)-3-azidocyclopentane.

11. A compound of claim 1, wherein the compound is (1R,3R)-TRANS-1-(9-adenyl)-3-azidocyclopentane hydrochloride.

12. A compound of claim 1, wherein the compound is (1R,3R)-TRANS-1-(9-adenyl)cyclopentane-3-thiol or salt thereof.

13. A compound of claim 1, wherein the compound is (1R,3R)-TRANS-1-(9-adenyl)-3-aminocyclopentane or salt thereof.

14. A compound of the formula

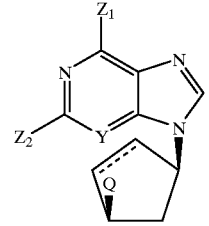

wherein

Q is methanesulfonate, trifluoromethanesulfonate, p-toluenesulfonate, 2-nitrobenzenesulfonate, 3-nitrobenzenesulfonate, 4-nitrobenzenesulfonate or 4-bromobenzenesulfonate;

Q is in the CIS configuration relative to the bicyclic substituent;

Y is nitrogen;

$Z_1$ and $Z_2$ are each independently hydrogen, halogen or $NH_2$; and

---- represents a single or double bond;

or a pharmaceutically acceptable salt thereof.

15. The composition according to claim 2, wherein $Z_2$ is hydrogen.

16. A compound according to claim 14, wherein $Z_2$ is hydrogen.

17. A compound according to claim 16, wherein $Z_1$ is $NH_2$.

18. A compound of claim 14, wherein the compound is (1R,3S)-CIS-1-(9-adenyl)-3-methanesulfoxycyclopentane.

19. The composition according to claim 2, wherein $Z_1$ is $NH_2$.

20. The composition according to claim 2, wherein X is selected from the group consisting of $N_3$, $NH_2$, NHR, $N(R)_2$, CN, SH, SR and $OR_1$ and R is $C_1$–$C_4$ alkyl.

21. The composition according to claim 2, wherein X is $NH_2$.

22. The composition according to claim 20, wherein $Z_2$ is hydrogen.

* * * * *